(12) United States Patent
Saltel et al.

(10) Patent No.: US 11,806,433 B2
(45) Date of Patent: Nov. 7, 2023

(54) ALCOHOL-RESISTANT ORAL PHARMACEUTICAL COMPOSITIONS OF LORAZEPAM

(71) Applicant: EDGEMONT PHARMACEUTICALS, LLC TRUST, Newark, NJ (US)

(72) Inventors: Douglas Saltel, Austin, TX (US); Michael Vachon, Austin, TX (US)

(73) Assignee: EDGEMONT PHARMACEUTICALS, LLC TRUST, Newark, NJ (US)

(*) Notice: Subject to any disclaimer, the term of this patent is extended or adjusted under 35 U.S.C. 154(b) by 162 days.

(21) Appl. No.: 16/753,487

(22) PCT Filed: Oct. 25, 2018

(86) PCT No.: PCT/US2018/057433
§ 371 (c)(1),
(2) Date: Apr. 3, 2020

(87) PCT Pub. No.: WO2019/089330
PCT Pub. Date: May 9, 2019

(65) Prior Publication Data
US 2020/0375906 A1    Dec. 3, 2020

Related U.S. Application Data

(60) Provisional application No. 62/580,321, filed on Nov. 1, 2017.

(51) Int. Cl.
*A61K 9/20*     (2006.01)
*A61K 31/5513*  (2006.01)
(Continued)

(52) U.S. Cl.
CPC ............ *A61K 9/2081* (2013.01); *A61K 9/009* (2013.01); *A61K 9/1652* (2013.01);
(Continued)

(58) Field of Classification Search
CPC .. A61K 9/2072; A61K 9/2081; A61K 9/5021; A61K 9/5036; A61K 9/5047; A61K 31/5513; A61K 9/5073
See application file for complete search history.

(56) References Cited

U.S. PATENT DOCUMENTS 5,891,474 A * 4/1999 Busetti ................ A61K 9/2886
424/490
8,999,393 B1   4/2015 Saltel et al.
(Continued)

FOREIGN PATENT DOCUMENTS

EA       015615 B1   10/2011
FR    2897267 A1    2/2006
(Continued)

OTHER PUBLICATIONS

Chemical Book (https://www.chemicalbook.com/ChemicalProductProperty_EN_CB3735028.html). 5 pages (Year: 2017).*
(Continued)

*Primary Examiner* — Lakshmi S Channavajjala
(74) *Attorney, Agent, or Firm* — CANTOR COLBURN LLP

(57) ABSTRACT

Described herein are alcohol-resistant oral pharmaceutical compositions and dosage forms that exhibit reduced drug release in the presence of alcohol. The compositions comprise a substrate comprising a controlled release formulation of lorazepam and an alcohol-resistant coating surrounding the substrate.

25 Claims, 3 Drawing Sheets

(51) Int. Cl.
*A61K 9/50* (2006.01)
*A61K 9/00* (2006.01)
*A61K 9/16* (2006.01)

(52) U.S. Cl.
CPC .......... *A61K 9/5036* (2013.01); *A61K 9/5047* (2013.01); *A61K 31/5513* (2013.01)

(56) References Cited

U.S. PATENT DOCUMENTS

| | | |
|---|---|---|
| 2011/0223244 A1 | 9/2011 | Liversidge et al. |
| 2014/0271896 A1 | 9/2014 | Abu Shmeis et al. |

FOREIGN PATENT DOCUMENTS

| | | |
|---|---|---|
| WO | 2006079550 A2 | 8/2006 |
| WO | 2007048220 A2 | 5/2007 |
| WO | 2009076764 A1 | 6/2009 |
| WO | 2012085656 A2 | 6/2012 |
| WO | 2014110245 A1 | 1/2014 |
| WO | 2014110248 A1 | 7/2014 |
| WO | 2014144027 A1 | 9/2014 |
| WO | 2016193034 A1 | 12/2016 |

OTHER PUBLICATIONS

Carbomer—an overview | ScienceDirect Topics, https://www.sciencedirect.com/topics/medicine-and-dentistry/carbomer. 7 pages, Dec. 16, 2022 (Year: 2022).*

International Search Report for International Application No. PCT/US2018/057433, International Filing Date Oct. 25, 2018, dated Feb. 1, 2019, 7 pages.

Written Opinion for International Application No. PCT/US2018/057433, International Filing Date Oct. 25, 2018, dated Feb. 1, 2018, 10 pages.

A.C. Van Der Vossen et al., "Formulating a poorly water soluble drug into an oral solution suitable for paediatric patients; lorazepam as a model drug", European Journal of Pharmaceutical Sciences, vol. 100, 2017, pp. 205-2010.

A.T. Burbello, Contemporary medicines: Clinical and Pharmacological Handbook of a Practical Physician, OLMA-Press 2003 p. 593; Entry for "Lorazepam," a tranquilizer from the group of benzodiazepine derivatives used for neuroses, psychopathy, neurosis-like disorders and sleep disorders.

Adeline Siew, "Dissolution Testing", Pharmaceutical Technology, vol. 40, Issue 11, Nov. 2, 2016, 4 pages.

Japanese Pharmaceutical Excipients Directory 2016, Feb. 18, 2016, vol. 29, No. 30, pp. 122-125.

K.V. Alekseev et al. "Excipients in the Technology of Modified-Release Tablets" Pharmacy Journal No. 6 (2009) pp. 49-56; The paper characterizes modified-release tablets and describes excipients used in their manufacture.

The Chemical Encyclopedic Dictionary, Edited by I. L. Knunyants_ Moscow, USSR, 1983, selected pages; Chemical Encyclopedic Dictionary entry for "alcohol".

V.L. Bagirova et al., "Modern aspects of the use of excipients in the technology of pharmaceuticals", Pharmateca, No. 6, 1998, pp. 34-36.

* cited by examiner

ALCOHOL-RESISTANT ORAL PHARMACEUTICAL COMPOSITIONS OF LORAZEPAM

FIELD

Described herein are alcohol-resistant controlled release oral pharmaceutical compositions of lorazepam that exhibit reduced drug release in the presence of alcohol.

BACKGROUND

Many drugs have deleterious effects when consumed in conjunction with alcohol. Additionally, some controlled release formulations are susceptible to abuse by using alcohol to alter the controlled release drug delivery profile to achieve more immediate release. Intentional or inadvertent tampering with oral pharmaceutical formulations can result in rapid delivery of a massive dose of drug which may be associated with serious and life-threatening side effects, including respiratory depression, respiratory failure, sedation, cardiovascular collapse, coma and death.

Various approaches have been developed to prevent alcohol tampering or alcohol abuse with controlled release formulations, but there remains a need for alcohol-resistant oral pharmaceutical dosage forms of lorazepam.

SUMMARY

Provided herein, in one aspect, are alcohol-resistant oral pharmaceutical compositions, comprising a coated substrate comprising a substrate comprising a controlled release lorazepam formulation surrounded by an alcohol-resistant coating. In some embodiments, the amount of lorazepam released from the coated substrate is 75% or less, 50% or less, 25% or less, 10% or less, or 1% or less, than the amount of lorazepam released from the uncoated substrate, when measured by dissolution testing at 37.0±0.5° C. and 100 rpm for two hours in an acidic ethanolic aqueous solution comprising 40% ethanol and 0.1 N HCl solution in accordance with USP <711>.

In some embodiments, the alcohol-resistant coating comprises one or more ethanol-insoluble components selected from the group consisting of ethanol-insoluble polymeric polysaccharides, polymeric ethers, polymeric alcohols, polymeric carboxylic acids, polymeric carboxylic acid esters, and polymeric carboxylic acid alcohols. In some embodiments, the alcohol-resistant coating comprises one or more ethanol-insoluble components selected from the group consisting of ethanol-insoluble carbomers, polyethylene oxide polymers, xanthan gum, and alginate. In some embodiments, the alcohol-resistant coating comprises sodium carboxymethylcellulose. In some embodiments, the alcohol-resistant coating comprises xanthan gum. In some embodiments, the weight:weight ratio of alcohol-resistant coating to substrate of the coated substrate is at least 1:10, from 1:10 to 3:1, from 1:10 to 1:1, or any ratio there between.

In some embodiments, the amount of lorazepam released from the coated substrate is ±50% or less, ±40% or less, ±30% or less, ±25% or less, ±20% or less, ±10% or less, ±5% or less, or ±1% or less, as compared to the amount of lorazepam released from a corresponding substrate without the alcohol-resistant coating, when measured by dissolution testing at 37.0±0.5° C. and 100 rpm for two hours in an aqueous 0.1 N HCl solution, in accordance with USP <711>.

In some embodiments, concomitant consumption of lorazepam with alcohol is associated with a clinical risk.

In some embodiments, the substrate is in a form selected from the group consisting of particles, granules, pellets, and beadlets. In some embodiments, the substrate is in a form selected from the group consisting of tablets and capsules. In some embodiments, the substrate comprises a controlled release formulation of lorazepam. In some embodiments, the composition or dosage form additionally includes an immediate release formulation of lorazepam, which optionally may be a substrate provided with an alcohol-resistant coating. In some embodiments, the controlled release formulation is a delayed release formulation, a sustained release formulation, or a delayed sustained release formulation. In some embodiments, the coated substrate comprises a delayed-release coating disposed between the substrate and the alcohol-resistant coating. In some embodiments, the coated substrate comprises the alcohol-resistant coating disposed between the substrate and a delayed-release coating. In some embodiments, the coated substrate is formulated in a tablet or filled into a capsule shell, wherein the tablet or capsule shell optionally is surrounded by an alcohol-resistant coating. In some embodiments, the substrate is in the form of a tablet or capsule surrounded by an alcohol-resistant coating. In some embodiments, the coated substrate is contained within a sachet package.

Provided herein, in another aspect, are alcohol-resistant oral pharmaceutical compositions of lorazepam, comprising (A) coated sustained release beadlets comprising (i) beadlets comprising lorazepam in a sustained release formulation surrounded by an alcohol-resistant coating, wherein the alcohol-resistant coating is less soluble in ethanol than in water; and (B) coated delayed sustained release beadlets comprising (i) beadlets comprising lorazepam in a sustained release formulation, (ii) an enteric coating surrounding the beadlets, and (iii) an alcohol-resistant coating surrounding the beadlets, wherein the alcohol-resistant coating is less soluble in ethanol than in water, and wherein the alcohol-resistant coating may be interior to or exterior to the enteric coating.

Provided herein, in another aspect, are alcohol-resistant oral pharmaceutical compositions of lorazepam, comprising (A) sustained release beadlets comprising lorazepam in a sustained release formulation; and (B) delayed sustained release beadlets comprising (i) beadlets comprising lorazepam in a sustained release formulation, (ii) an enteric coating surrounding the beadlets, formulated in a capsule or tablet, wherein the capsule or tablet is surrounded by an alcohol-resistant coating, wherein the alcohol-resistant coating is less soluble in ethanol than in water, and wherein the alcohol-resistant coating may be interior to or exterior to the enteric coating.

Provided herein, in another aspect, are methods of reducing the risks of concomitant consumption of lorazepam and alcohol, comprising administering an alcohol-resistant oral pharmaceutical composition of lorazepam as described herein to a subject in need thereof.

Provided herein, in another aspect, are methods of inhibiting alcohol extraction of lorazepam from an oral pharmaceutical composition, comprising preparing an alcohol-resistant oral pharmaceutical composition of lorazepam as described herein.

As shown in the figure, in some embodiments, alcohol-resistant oral pharmaceutical dosage forms as described herein are in the form of a tablet or capsule (100) that comprises particles, granules, pellets, beadlets, etc. (10) comprising active agent ("API") (e.g., lorazepam), wherein individual particles, granules, pellets, beadlets, etc. (10) are provided with an optional alcohol-resistant coating (12). Additionally or alternatively, in some embodiments, the tablet or capsule is provided with an alcohol-resistant coating (102). As depicted in the figure, the dosage form may include controlled release formulations and, optionally, immediate release formulations, depending on the composition of the particles, granules, pellets, beadlets, etc. (10), any additional coatings provided on the particles, granules, pellets, beadlets, etc., the composition of any tablet or capsule matrix (104), and/or any additional coatings provided on the tablet or capsule (100).

Figure 2:
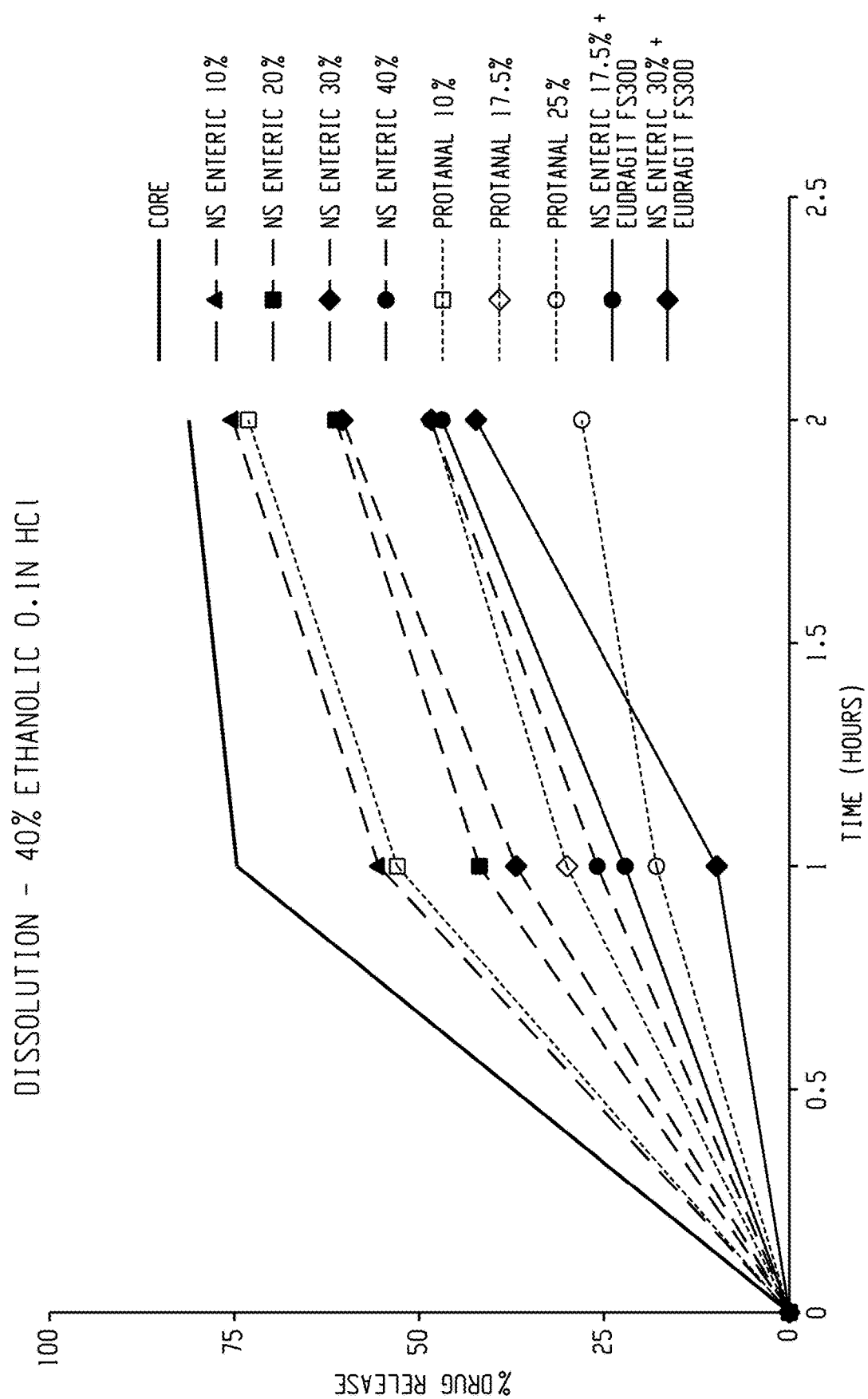

FIG. 2 illustrates the results of dissolution testing described in Example 3.

Figure 3:
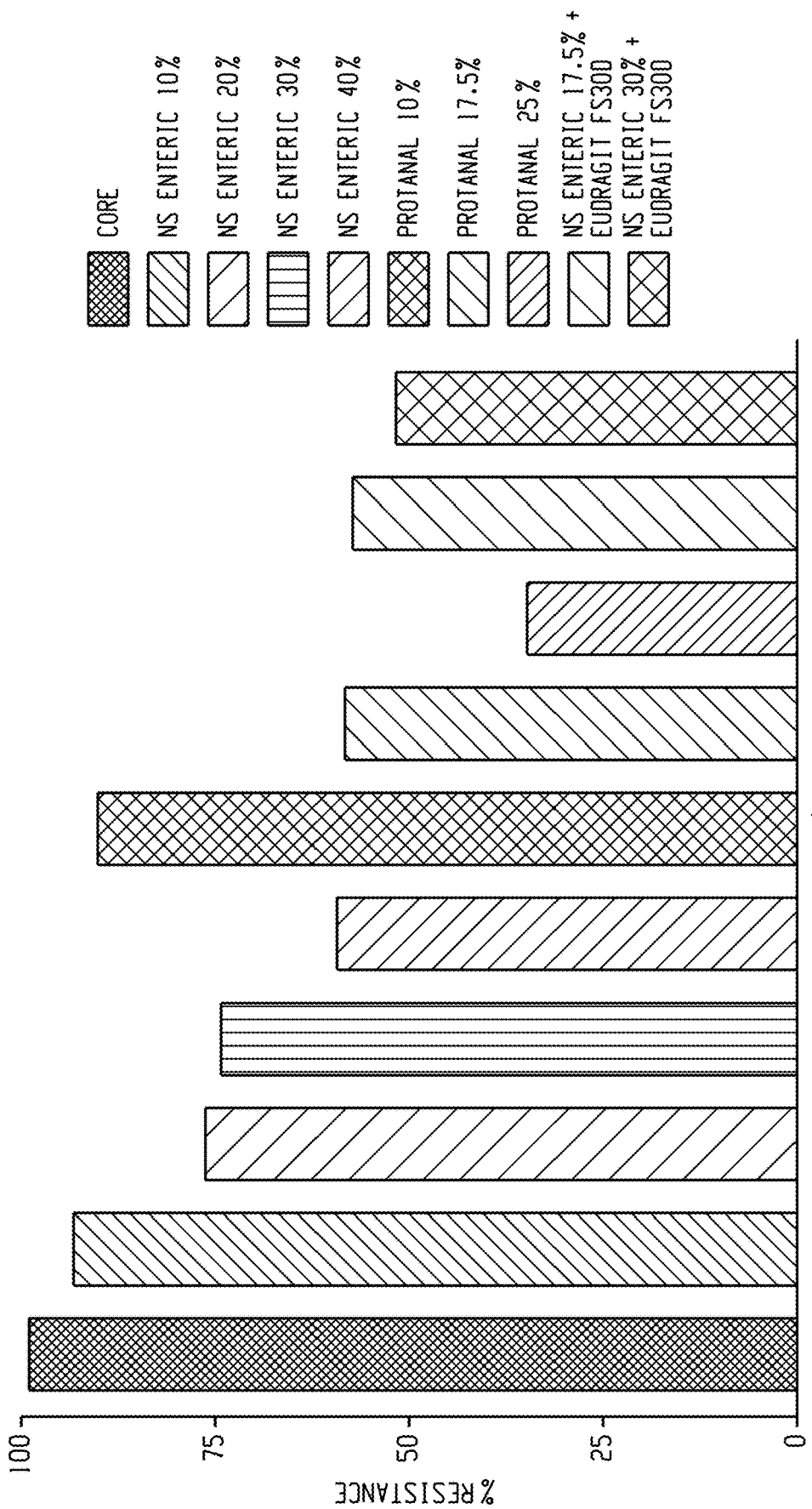

FIG. 3 illustrates the results of dissolution testing described in Example 3 and reports drug release of alcohol-resistant coated compositions as described herein relative to an uncoated substrate.

DETAILED DESCRIPTION

Described herein are alcohol-resistant oral pharmaceutical compositions and dosage forms that exhibit reduced drug release in the presence of alcohol. In broad terms, the compositions comprise a substrate comprising a controlled release lorazepam formulation that is coated with an alcohol-resistant coating. In specific embodiments, the amount of lorazepam released from the coated substrate in the presence of alcohol is 75% or less than the amount of lorazepam released from the uncoated substrate in the presence of alcohol, when measured by dissolution testing at 37.0±0.5° C. and 100 rpm for two hours in an acidic ethanolic aqueous solution comprising 40% ethanol and 0.1 N HCl solution, such as in accordance with USP <711>.

Various embodiments are described hereinafter. It should be noted that the specific embodiments are not an exhaustive description of the invention described herein and do not limit broader aspects of the invention. Moreover, although various aspects may be discussed in specific combinations or configurations, it should be understood that any aspect can be used in any permutation or combination with other aspects described herein.

Unless otherwise stated, the following terms used in the specification and claims have the meanings given below:

The use of the terms "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. The use of any and all examples and exemplary language (e.g., "such as") is illustrative only on not limiting.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

All methods described herein can be performed in any suitable order unless otherwise indicated herein or otherwise clearly indicated by context.

As used herein, the terms "pharmaceutically active agent," "active agent" and "drug" are used interchangeably to refer to lorazepam.

As used herein, the term "controlled release formulation" means a formulation designed to provide sustained and/or delayed release of lorazepam. As used herein, the term "sustained release formulation" means a formulation designed to release lorazepam slowly, over an extended time period. Non-limiting examples of sustained release include release by gradual dissolution or disintegration of lorazepam-containing matrix, or by a passive diffusion or osmotic delivery system. As used herein, the term "delayed release formulation" means a formulation designed to release lorazepam after a time period or in a target region of the gastrointestinal tract, such as by erosion of an enteric coating, a pH-dependent coating, or a pH-independent coating.

As used herein, the term "immediate release formulation" means a formulation other than a controlled release formulation. In some embodiments, an immediate release formulation is formulated without any components designed to control or promote release. In other embodiments, an immediate release formulation is formulated to achieve rapid release of the lorazepam, such as by including a component that promotes dissolution or disintegration of a lorazepam-containing matrix upon ingestion.

As used herein, the term "unit dosage form" means the physical unit of a pharmaceutical composition administered to or ingested by the subject, such as a tablet, capsule, or a sachet containing particles, granules, pellets, beadlets, etc.

Some drugs become more potent and/or more dangerous when mixed with alcohol or when used in conjunction with alcohol. Additionally or alternatively, a subject may mix a drug with alcohol or use a drug in conjunction with alcohol in an attempt to achieve faster release from a controlled release formulation. Many controlled release formulations are susceptible to such "dose dumping" in the presence of alcohol due to the solubility of components used to provide controlled release (e.g., controlled release polymer(s)) in alcohol. Various approaches have been developed to address risks associated with alcohol-induced dose-dumping, but the goal of these approaches is to achieve the same dissolution profile in the presence or absence of alcohol. Prior to the present invention, approaches have not been described for achieving reduced release in the presence or absence of alcohol. Moreover, prior to the present invention, approaches have not been described that are useful for all types of formulations, including immediate release as well as controlled release formulations.

As noted above, described herein are alcohol-resistant oral pharmaceutical compositions and dosage forms that exhibit reduced release of lorazepam in the presence of alcohol. The compositions and dosage forms can be used with any type of formulation, including various controlled release formulations, and, optionally, additionally including immediate release formulation component. When an alcohol-resistant oral pharmaceutical composition or dosage form as described herein is ingested in conjunction with concomitant use of alcohol, the composition or dosage form exhibits reduced release of lorazepam, such as by exhibiting a slower release rate and/or releasing a reduced amount of lorazepam. This approach is different than approaches designed to address alcohol resistant dose-dumping, because in those approaches the goal often is to exhibit substantially the same release of drug in the presence of alcohol as obtained in the absence of alcohol.

Alcohol-Resistant Oral Pharmaceutical Dosage Forms

As noted above, in broad terms, the alcohol-resistant compositions and dosage forms described herein comprise a substrate comprising a controlled release lorazepam formulation that is coated with an alcohol-resistant coating surrounding the substrate. In some embodiments, the coated substrate is a discrete particle, granule, beadlet (etc.) that may be formulated in a larger matrix (such as a tablet or capsule matrix) or contained in a capsule or sachet. In other embodiments, the coated substrate is a unit dosage form, such as a coated tablet or coated capsule. In some embodiments, both discrete particles, granules, granules, pellets, beadlets, etc. formulated in a unit dosage form and the unit dosage form itself are provided with an alcohol-resistant coating, which may be the same or different. For example, in some embodiments, the dosage form is in the form of a tablet wherein coated lorazepam particles, granules, granules, pellets, beadlets, etc. (each surrounded by an alcohol-resistant coating) are dispersed in a tablet matrix. Optionally, the tablet as a whole is provided with an alcohol-resistant coating. Alternatively, only the tablet as a whole (and not the lorazepam particles, granules, granules, pellets, beadlets, etc.) is provided with an alcohol-resistant coating. In other embodiments, the dosage form is in the form of a capsule, wherein coated lorazepam particles, granules, granules, pellets, beadlets, etc. (each surrounded by an alcohol-resistant coating) are contained within a capsule shell. Optionally, the capsule as a whole is provided with an alcohol-resistant coating. Alternatively, only the capsule as a whole (and not the particles, granules, granules, pellets, beadlets, etc.) is provided with an alcohol-resistant coating. In other embodiments, the dosage form is in the form of a sachet containing lorazepam particles, granules, granules, pellets, beadlets, etc. (each surrounded by an alcohol-resistant coating) are contained within a sachet package.

For convenience, lorazepam-containing particles, granules, beadlets, etc., are referred to in the following discussion as a "drug-containing core." The drug-containing core may include any type of drug-containing core, including those known in the art, including a core that comprises a controlled release formulation of lorazepam. In some embodiments, the composition or dosage form may additionally include a core that comprises an immediate release formulation of lorazepam or a core that consists of lorazepam. In accordance with any embodiments, the drug-containing core may be provided with a coating typically used in oral pharmaceutical formulations, such as a sustained-release coating or a delayed release coating, including an enteric coating, a pH-dependent coating, and/or a pH-independent coating, a flavor coating, a seal coating, etc. In accordance with any embodiments, the composition or dosage form may include one or more different types of drug-containing cores, such as any one or two or more controlled release cores, or any combination of any one or more immediate release cores and any one or more controlled release cores. Thus, the alcohol-resistant technology disclosed herein can be applied to any controlled release oral pharmaceutical formulations of lorazepam, to reduce the clinical risk associated with concomitant consumption of alcohol and/or inhibit alcohol extraction.

The compositions and dosage forms may be prepared by conventional methodologies, including those discussed below with reference to specific embodiments. For example, tablets can be prepared by direct compression of the drug-containing cores, capsules can be prepared by filling drug-containing cores into capsules, and sachets can be prepared by filling drug-containing cores into sachet packages.

Alcohol-Resistant Coatings

As noted above, the compositions and dosage forms described herein comprise a substrate comprising a controlled release formulation of lorazepam that is coated with an alcohol-resistant coating surrounding the substrate. In some embodiments, the alcohol-resistant coating comprises one or more ethanol-insoluble components. As used herein, "ethanol-insoluble component" refers to a component that exhibits a relative solubility in ethanol of at most 60%, such as a relative solubility of 60% or less, 55% or less, 50% or less, 45% or less, 40% or less, 35% or less, 30% or less, 35% or less, 30% or less, 25% or less, 20% or less, 15% or less, 10% or less, 5% or less, 1% or less, or is essentially insoluble in ethanol. In specific embodiments, the ethanol-insoluble component exhibits a relative solubility in ethanol of 20% or less. In other specific embodiments, the ethanol-insoluble component exhibits a relative solubility in ethanol of 15% or less. In further specific embodiments, the ethanol-insoluble component exhibits a relative solubility in ethanol of 10% or less. As used herein, the term "relative solubility of X %" means that at most X % w/v of the component dissolves in ethanol when measured at room temperature by a saturation shake-flask method.

In some embodiments, the alcohol-resistant coating includes one or more ethanol-insoluble polymers as an ethanol-insoluble component. Examples of ethanol-insoluble polymers include, but are not limited to, ethanol-insoluble polysaccharides (e.g., cellulosics), polymeric ethers, polymeric alcohols, polymeric carboxylic acids, polymeric carboxylic acid esters, and polymeric carboxylic acid alcohols. More specific examples of ethanol-insoluble polymers include ethanol-insoluble carbomers, polyethylene oxide polymers, xanthan gum, alginate, and polyvinyl alcohol derived from polyvinyl acetate.

In specific embodiments, the alcohol-resistant coating includes as an ethanol-insoluble component alginate, such as sodium alginate, alginate in other salt forms, alginate in a non-ionic form, and any combinations thereof. In further specific embodiments, the alcohol-resistant coating includes sodium alginate. Non-limiting examples of commercially available ethanol-insoluble sodium alginate products include PROTANAL® CR 8133 (FMC Corporation), PROTANAL® LFR5/60 (FMC Corporation), and NS ENTERIC® (Colorcon).

Additionally or alternatively, the alcohol-resistant coating may include as an ethanol-insoluble component carboxymethylcellulose, such as sodium carboxymethylcellulose. A non-limiting example of a commercially available ethanol-insoluble sodium carboxymethylcellulose product is OPA-GLOS® 2 (Colorcon), which also contains maltodextrin, dextrose monohydrate, and stearic acid.

Additionally or alternatively, the alcohol-resistant coating may include as an ethanol-insoluble component xanthan gum.

The alcohol-resistant coating is applied to the substrate in an amount effective to confer alcohol-resistance to the resulting coated substrate. In some embodiments, the weight:weight ratio of alcohol-resistant coating to substrate of the coated substrate is at least 1:10. This includes weight:weight ratios of alcohol-resistant coating to substrate of at least 1:10, at least 1.5:10, at least 2:10, at least 2.5:10, at least 3:10, at least 3.5:10, at least 4:10, at least 4.5:10, at least 5:10, at least 5.5:10, at least 6:10, at least 6.5:10, at least 7:10, at least 7.5:10, at least 8:10, at least 8.5:10, at least 9:10, at least 9.5:10, and at least 1:1. In some embodiments, the weight:weight ratios of alcohol-resistant coating to substrate are selected from 1:10, 1:9, 1:8, 1:7, 1.5:10, 1:6, 1:5, 1:4, 3:10, 1:3, 3.5:10, 4:10, 4.5:10, 1:2, 5.5:10, 6:10, 6.5:10, 7:10, 7.5:10, 8:10, 8.5:10, 9:10, 9.5:10, 1:1, 2:1, and 3:1, including incremental ratios therein. In some embodiments, the weight:weight ratio of alcohol-resistant coating to substrate is from 1:10 to 3:1. In some embodiments, the weight:weight ratio of alcohol-resistant coating to substrate is from 1:10 to 2:1. In some embodiments, the weight:weight ratio of alcohol-resistant coating to substrate is from 1:10 to 1:1. In general, a greater weight:weight ratio of alcohol-resistant coating to substrate is correlated with greater alcohol resistance, but a very high amount of alcohol-resistant coating may impact the release profile of the coated substrate in non-alcohol environments, which may be undesirable, depending on the target properties for the composition.

As noted, in some embodiments, the coated substrate releases 75% or less of lorazepam from the substrate in the presence of alcohol as compared to the amount of lorazepam released from a corresponding substrate without the alcohol-resistant coating, when measured by dissolution testing at 37.0±0.5° C. and 100 rpm for two hours in an acidic ethanolic aqueous solution comprising 40% ethanol and 0.1 N HCl solution, in accordance with USP <711>. In some embodiments, the amount of lorazepam released from the coated substrate is 75% or less, 70% or less, 60% or less, 50% or less, 40% or less, 33% or less, 30% or less, 25% or less, 20% or less, 10% or less, 5% or less, or 1% or less, as compared to the amount of lorazepam released from a corresponding substrate without the alcohol-resistant coating.

Additionally or alternatively, in some embodiments, the alcohol-resistant coating does not substantially impact release of lorazepam from the substrate in a non-alcoholic environment as compared to the amount of lorazepam released from a corresponding substrate without the alcohol-resistant coating, such as when measured by dissolution testing at 37.0±0.5° C. and 100 rpm for two hours in an aqueous 0.1 N HCl solution, in accordance with USP <711>. In some embodiments, the amount of lorazepam released from the coated substrate is ±25% or less, ±20% or less, ±10% or less, ±5% or less, or ±1% or less, as compared to the amount of lorazepam released from a corresponding substrate without the alcohol-resistant coating, when measured by dissolution testing at 37.0±0.5° C. and 100 rpm for two hours in an aqueous 0.1 N HCl solution, in accordance with USP <711>. In other embodiments, the alcohol-resistant coating may impact release of lorazepam from the substrate in a non-alcoholic environment. For example, in some embodiments, the amount of lorazepam released from the coated substrate is ±50% or less, ±40% or less, ±30% or less, as compared to the amount of lorazepam released from a corresponding substrate without the alcohol-resistant coating, when measured by dissolution testing at 37.0±0.5° C. and 100 rpm for two hours in an aqueous 0.1 N HCl solution, in accordance with USP <711>.

Exemplary Immediate Release Formulations

In specific embodiments, the controlled release compositions and dosage forms additionally include a drug-containing core comprising an immediate release form of lorazepam, such as a core that consists of lorazepam or an immediate release formulation of lorazepam, such as lorazepam formulated in an immediate release composition. Immediate release formulations are known in the art. In some embodiments, an immediate release formulation is formulated without any components designed to control or promote release. In other embodiments, an immediate release formulation is formulated to achieve rapid release of the lorazepam, such as by including a component that promotes dissolution or disintegration of a lorazepam-containing composition upon ingestion, such as a superdisintegrant such as cross-linked polyvinylpyrrolidone (crospovidone), croscarmellose sodium, sodium starch glycolate, carboxymethylcellulose, etc.

In specific embodiments, an immediate release formulation releases at least 70% of the lorazepam within 60 minutes of ingestion, within 30 minutes of ingestion, or within 15 minutes of ingestion. In specific embodiments, an immediate release formulation releases at least 80% of the lorazepam within 60 minutes of ingestion, within 30 minutes of ingestion, or within 15 minutes of ingestion. In specific embodiments, an immediate release formulation releases at least 90% of the lorazepam within 60 minutes of ingestion, within 30 minutes of ingestion, or within 15 minutes of ingestion.

In some embodiments, an alcohol-resistant oral composition or dosage form comprises, in addition to a substrate comprising a controlled release formulation of lorazepam, a substrate comprising an immediate release formulation of lorazepam and an alcohol-resistant coating surrounding the substrate.

Exemplary Controlled Release Formulations

In specific embodiments, the compositions or dosage forms include a drug-containing core comprising a controlled release form of lorazepam, such as lorazepam formulated in a sustained release composition and/or provided with a sustained release and/or delayed release coating. Controlled release formulations and coatings are known in the art.

Exemplary Sustained Release Core Formulations

In specific embodiments, a sustained release core comprises lorazepam formulated in a sustained release composition or provided with a sustained release barrier coating.

Typical polymers used in sustained release formulations include various grades of gelling polymers such as hydroxypropyl methylcellulose (HPMC), polyacrylates such as various EUDRAGIT® brand compositions (such as EUDRAGIT® RS PO (poly(ethyl acrylate-co-methyl methacrylate-co-trimethylammonioethyl methacrylate chloride) 1:2:0.1; powder product) (Evonik Industries), polyvinyl alcohols, and polyethylene oxides. Blends of gelling polymers of the same class having different molecular weights and/or different degrees of cross-linking, viscosity, etc., can be used. A sustained release formulation also may include non-gelling polymers to achieve the desired release and pharmacokinetic properties.

When PEO is used in a sustained release composition, it typically has an average (approximate) molecular weight of at least 900,000 and usually not greater than 5,000,000. Commercially available PEO polymers include POLYOX™ (Dow Chemical Corp.) that have average molecular weights up to 7,000,000. Higher molecular weight PEO polymers generally result in slower release rates. Higher concentrations of PEO also tend to decrease the rate of release. Thus, the desired release and pharmacokinetic properties can be selected and controlled by selecting and controlling the average molecular weight of the PEO polymer(s) used and the relative amount thereof. Typically, sustained release cores are formed with PEO having an average molecular weight of between about 900,000 and about 4,000,000, including from about 900,000 to about 2,000,000.

The amount of gelling polymer in a sustained formulation is typically from about 20% to about 70% of the core, including from about 30% to about 60% by weight. When the polymer is primarily (or exclusively) PEO having an average molecular weight of from 900,000 to 1,500,000, the amount of polymer may be in the range of from about 35 to about 55%, including from about 40% to about 50%. As noted above, polymers having higher average molecular weights may be used in lower amounts, such as from about 20% to about 50%, including from about 25% to about 45%.

Sustained release formulations are generally made by granulating and extruding a mixture comprising the polymer material(s), lorazepam, and optionally additional excipients such as binders and fillers. Binders and fillers include starch, microcrystalline cellulose (MCC), etc. The extruded cores are typically subject to spheronization and drying.

Barrier coating-based cores may be made using a nonpareil seed core, such as a sugar core or MCC core, upon which successive functional coating layers are formed. For instance, a core could be coated with a sealing coat, followed by a drug layer coat having lorazepam and a binder, followed by a release-controlling polymer coat layer (the barrier layer). The barrier layer may be, for example, a water insoluble polymer such as a film-forming material. Examples include celluloses such as ethyl cellulose and acrylate polymers and copolymers. Additional materials may be included to enhance performance of the film. These include but are not limited to plasticizer(s) to confer flexibility and ensure that coat cracking or physical changes do not compromise the drug releasing properties; anti-tacking aids to minimize particle adherence/aggregation during processing or storage; dispersants/wetting agents to aid in surface coating; and pore formers where indicated to provide channels for drug release.

In some embodiments, a sustained release core exhibits substantially zero order release of 90% by weight of lorazepam over about 7 to about 12 hours, when tested by in vitro dissolution testing as illustrated in the examples, such as in a USP Type I apparatus (Basket) using 0.1 N HCl as the dissolution media. For clarity, such sustained release cores do not achieve 90% release of lorazepam until 7 hours or later, when tested by in vitro dissolution testing as illustrated in the examples. For example, in accordance with some embodiments, not more than 40% of lorazepam is released at 2 hours when tested by in vitro dissolution testing as discussed in the examples, including not more than 35%, not more than 30%, or not more than 25%. In specific embodiments, a sustained release core provides therapeutic effect for 24 hours under steady state conditions with daily dosing. In specific embodiments, a sustained release core achieves a Tmax not sooner than 6 hours after administration, including not sooner than 8 hours, or not sooner than 10 hours after administration.

Other Core Components

In addition to lorazepam and any controlled release polymer, a drug-containing core may include other excipients, such as diluents and lubricants. Diluents provide bulk and can enhance physical properties, such as tableting or tablet properties. Examples of suitable diluents include sugars such as lactose or mannitol; microcrystalline cellulose; and calcium phosphates such as dibasic calcium phosphate dihydrate, dibasic calcium phosphate anhydrous, and tribasic calcium phosphate. Diluents typically comprise from about 30% to about 70% by weight of a core particle. Lubricants include magnesium stearate and sodium stearyl fumarate. Lubricants, when present, typically comprise from about 1% to about 3% by weight of a core particle. For example, a core may include lactose (such as 10 to 50% or 20 to 40% by weight lactose monohydrate) and calcium phosphate (such as 10 to 50% or 20 to 40% by weight dibasic calcium phosphate) as diluents.

Exemplary Delayed Release Coatings

As noted above, a drug-containing core may be provided with a delayed release coating, such as an enteric coating, a pH-dependent coating, or a pH-independent coating. A delayed release coating typically delays release of lorazepam from the core until the coating has sufficiently dissolved to expose the core to the environment of the gastrointestinal tract or become sufficiently permeable for lorazepam to pass through the remaining coating. For example, a delayed release coating may be designed to delay release in vivo until at least 3 hours after administration, such as to provide release at 4-8 hours after administration. A delayed release coating may be provided on an immediate release core or on a sustained release core.

Materials suitable for use in delayed release coatings are known in the art and include those based on pH, solubility, or a combination thereof. A pH-dependent coating, also known as an enteric coating, exhibits different solubility depending on the pH of the environment. At low pH, such as found in the stomach, an enteric coating is insoluble or substantially insoluble, and prevents release of lorazepam from the core. At higher pH, such as found in the intestines, an enteric coating is more soluble and dissolves and/or becomes permeable, thereby permitting body fluids to reach the core and release lorazepam from the core. In such coatings, the specific delayed release provide can be controlled by the pH at which the coating becomes soluble and by the coating thickness/amount applied. A solubility-based coating comprises a material with a low water-solubility that slowly dissolves or erodes in the environment of the gastrointestinal tract. In such coatings, the specific delayed release provide can be controlled by the solubility of the coating and the thickness/amount applied. Coating having components exhibiting both features also can be used. For clarity, a delay coating that has both pH-dependent polymers and pH-independent polymers is considered to be a pH-dependent delayed release coating.

Suitable polymers for pH-dependent delayed release coatings include those having free acid groups such as cellulose acetate phthalate or polymethacrylates and their copolymers. A useful enteric coating can be based on EUDRAGIT® FS 30 D (poly(methyl acrylate-co-methyl methacrylate-co-methacrylic acid) 7:3:1; 30% aqueous dispersion) (Evonik Industries). Other suitable enteric coating materials include EUDRAGIT® S 100 (poly(methacylic acid-co-methyl methacrylate) 1:2; powder product) (Evonik Industries) and EUDRAGIT® S 12.5 (poly(methacylic acid-co-methyl methacrylate) 1:2; 12.5% organic solution) (Evonik Industries). Enteric coatings can be based on a single enteric polymer or a combination and typically further contain a plasticizer. In the GI tract, the pH gradually increases in the small intestine from pH 6 to about pH 7.4 in the terminal ileum. Generally, an enteric coating is designed to release lorazepam at pH 7 or greater, including at about pH 7.4. As used herein, EUDRAGIT® FS 30 D is suitable for providing an enteric coating "designed to release at pH 7 or higher."

Suitable polymers for pH-independent delayed release coatings include water-soluble polymers that dissolving during GI transit, or water-insoluble polymers which swell under physiological conditions whereupon release of lorazepam is controlled by diffusion through the swollen coating. Examples of suitable polymers include cellulose acetates, ethylcellulose, glycerides, substituted methacrylates, polyvinyl acetate, HPMC, and carboxymethylcelluloses (CMC). Examples of water soluble polymers include cellulose ethers such as HPMC, methylcellulose, hydroxyethylcellulose, Na CMC, and polyvinylpyrrolidone (PVP). Less soluble or insoluble polymers include ethylcellulose and polymethacrylates. In some embodiments the coating contains a polymer having low water solubility which slowly dissolves away. In other embodiments, the coating contains a mixture of water-soluble and water-insoluble polymers (or polymers with higher and lower water solubility). The delayed release profile may be influenced by the water solubility, hydrophilic and swelling properties of the polymer(s) and coating thickness.

A delayed release coating can be provided by conventional means, such as by coating with a liquid coating composition and drying.

Delayed release properties can be assessed using a "two media dissolution test." In a "two media dissolution test," the first two hours are carried out using a media that comprises 0.1 N HCl. At 2 hours, the media is changed to a media that comprises a phosphate buffer and has a pH of 7.4. As is understood in the art, the first media approximates the stomach conditions while the second media approximates the intestinal conditions. When assessed in a two media in vitro dissolution test as described above, a pH-dependent delayed release coating will exhibit release shortly after the changeover to the pH 7.4 media, while a solubility-based delayed release coating that is not pH-dependent will not be as affected by the media changeover. Other ingredients can be present in the media, such as enzymes, etc., as is known in the art, e.g., in formulating simulated intestinal fluid (SIF). The two media dissolution test typically is conducted at 37° C. and can use 500 ml or 900 ml vessels. The stirring speed is typically 100 rpm, though the speed can be adjusted, such as to 75 or 50 rpm, etc., if necessary for the dissolution testing to give more useful information for a particular embodiment. For clarity, when options are provided such as different size vessels, a core that meets the profile release data under any option is considered to meet the release criteria; e.g., a core that exhibits at 2 hours 31% release in a 900 ml vessel but only 27% release in a 500 ml vessel is considered to meet the range of 30 to 50% release at 2 hours because it met the range in one of the options. The percentage of release at a point in time refers to the cumulative release up to that point in time, as per the conventional usage of these terms in the art. The amount of lorazepam released from the cores (i.e., dissolved into the dissolution media), can be determined by standard methods.

For delayed release coatings that are solubility-based and pH-independent, the release profile using the two media in vitro dissolution test generally shows 10% release not earlier than 2 hours and more typically not earlier than 4 hours and often at 6 hours or later. In some embodiments, a delayed sustained release core achieves 20 to 80% release, include 25-50% release, of lorazepam in 8 hours, and may not achieve 90% release until after 10 hours, or after 12 hours, but before 24 hours.

For delayed release coatings that are pH-dependent, the release profile using the two media in vitro dissolution test as described above, theoretically should exhibit no or essentially no release in the first media (e.g., for the first 2 hours). In practice, however, sometimes more lorazepam is released, such as 3%, or greater. Nevertheless, such coatings achieve appreciably greater release in the second media.

In specific embodiments where a substrate is provided with both a delayed-release coating and an alcohol-resistant coating, the delayed release coating and the alcohol-resistant coating may be applied in any order onto the substrate, such as the drug-containing core or unit dosage form. In specific embodiments, the delayed-release coating may be disposed between the substrate and the alcohol-resistant coating. In other specific embodiments, the alcohol-resistant coating is disposed between the substrate and delayed-release coating.

As noted above, compositions and dosage forms may comprise one or more of (i) a sustained release drug-containing core and (ii) a delayed release drug-containing core, and optionally may further comprise (iii) an immediate release drug-containing core, wherein one or more of the core types is surrounded by an alcohol-resistant coating, and/or where the dosage form as a whole is surrounded by an alcohol-resistant coating. Thus, in specific embodiments, the "substrate" for an alcohol-resistant coating as described herein may be one or more of (i) a sustained release drug-containing core and (ii) a delayed release drug-containing core, and, optionally (iii) an immediate release drug-containing core, and/or (iv) a dosage form as a whole (such as a tablet or capsule). In some embodiments, the dosage form as a whole (but not (i), (ii), or (iii) individually) is surrounded by an alcohol-resistant coating. In embodiments comprising more than one substrate, the alcohol-resistant coating provided on each substrate may be the same or different. In some embodiments, the alcohol-resistant coating provided on the drug-containing cores are the same while the alcohol-resistant coating provided on the dosage form as a whole, if present, is different. In some embodiments, the alcohol-resistant coating provided on the drug-containing cores and dosage form as a whole, if present, are the same. In some embodiments, the alcohol-resistant coating provided on the drug-containing cores and dosage form as a whole are different. In some embodiments, the same alcohol-resistant coating is provided on some of the drug-containing cores and the dosage form as a whole. Thus, in some embodiments, the alcohol-resistant coating on one or more of (i), (ii), (iii) and (iv) are the same. In some embodiments, the alcohol-resistant coating on one or more of (i), (ii), (iii), and (iv) are different.

Tablets and Capsules

As noted above, in some embodiments, an alcohol-resistant oral dosage form is in the form of a tablet. In some embodiments, the tablet is surrounded with an alcohol-resistant coating. In some embodiments, the tablet comprises lorazepam core particles that are coated with an alcohol-resistant coating, and the tablet is surrounded by an alcohol-resistant coating. In some embodiments, the tablet comprises lorazepam core particles that are not coated with an alcohol-resistant coating, and the tablet is surrounded by an alcohol-resistant coating. In some embodiments, the tablet comprises lorazepam core particles that are coated with an alcohol-resistant coating; and the tablet as a whole is not surrounded by an alcohol-resistant coating.

In some embodiments, an alcohol-resistant oral dosage form is in the form of a capsule. In some embodiments, the capsule is surrounded by an alcohol-resistant coating. In some embodiments, the capsule comprises lorazepam core particles that are coated with an alcohol-resistant coating and the capsule is surrounded by an alcohol-resistant coating. In some embodiments, the capsule comprises lorazepam core particles that are not coated with an alcohol-resistant coating and the capsule is surrounded by an alcohol-resistant coating. In some embodiments, the capsule comprises lorazepam core particles that are coated with an alcohol-resistant coating; and the capsule is not surrounded by an alcohol-resistant coating.

Exemplary Lorazepam Embodiments

In some embodiments, the alcohol-resistant oral composition or dosage form comprises a substrate comprising a controlled release formulation of lorazepam, wherein an alcohol-resistant coating surrounds the controlled release substrate, and optionally, additionally comprises a substrate comprising an immediate release formulation of lorazepam wherein an alcohol-resistant coating surrounds the immediate release substrate. In some embodiments, an alcohol-resistant oral dosage form comprises (i) a first substrate comprising a sustained release formulation of lorazepam; and/or (ii) a second substrate comprising a delayed sustained release formulation of lorazepam; and optionally further includes (iii) a third substrate comprising an immediate release formulation of lorazepam, wherein one or more of (i), (ii), and (iii) (if present) are surrounded by an alcohol-resistant coating. In some embodiments, the alcohol-resistant coating on one or more of (i), (ii), and (iii) are the same. In some embodiments, the alcohol-resistant coating on one or more of (i), (ii), and (iii) are different. In some embodiments, the alcohol-resistant oral dosage form as a whole is provided with an alcohol-resistant, which may be the same or different as any alcohol-resistant coating on (i), (ii), or (iii).

In specific embodiments, a dosage form as described herein contains from about 0.5 to about 10 mg lorazepam and achieves a pharmacokinetic profile that comprises a Tmax at 4 hours or later. Such a dosage form can provide a therapeutic effect for 24 hours (in steady state) when administered in a once daily dosing regimen. In specific embodiments, the dosage form achieves 20 to 80%, including 25 to 50%, release of lorazepam in 4 hours when tested in the two media dissolution test described above, and does not achieve 90% release until after 6 hours, after 8 hours, or after 10 hours. In specific embodiments, 50% of the lorazepam is released within 4 to 8 hours, while 70% release is not reached until 7 to 12 hours.

In specific embodiments, the alcohol-resistant oral pharmaceutical dosage form comprises lorazepam, and includes one or more of (A) sustained release particles comprising lorazepam in a sustained release formulation; and (B) delayed sustained release particles comprising a core comprising lorazepam in a sustained release formulation and an enteric coating surrounding the core, and, optionally, additionally includes (C) immediate release particles comprising lorazepam in an immediate release formulation, wherein one or more of (A), (B), and (C) (if present) are surrounded by an alcohol-resistant coating as described herein, and/or wherein the dosage form as a whole is surrounded with an alcohol-resistant coating as described herein.

A specific embodiment relates to a pharmaceutical composition that contains 2 mg of lorazepam for once daily dosing, split about evenly between sustained release particles and delayed sustained release particles, both provided with an alcohol-resistant coating. In some embodiments, all of the lorazepam present is present in the coated sustained release particles and delayed sustained release particles. In other embodiments, the dosage form additionally includes immediate release particles provided with an alcohol-resistant coating. Such a composition may provide a steady state Cmax of 26 ng/ml or less, including 23 ng/ml or less, when administered once daily. In some embodiments, the Cmin is at least about 10 ng/ml, at least about 11 ng/ml, or at least about 12 ng/ml, when the dosage form is administered once daily. Additionally or alternatively, in some embodiments, the Tmax may be within the range of about 4 to about 12 hours after once daily administration.

For clarity, the term "steady state" is used in its ordinary sense in the pharmaceutical arts. It does not mean constant, but rather refers to a dynamic equilibrium that is obtained after consistent successive administrations of lorazepam, typically after several days (e.g., 5 times the half-life, or 3-5 days in the case of lorazepam). For example, a patient already taking an immediate release formulation of lorazepam on a regular schedule (such as two or three times per day) already has the lorazepam in his/her blood when the next dose is administered. After ingestion, the dose is released and the amount of lorazepam in the blood increases to a maximum blood plasma concentration or "Cmax." The lorazepam is concurrently being metabolized and/or removed from the blood by biological actions of the body and so the blood plasma concentration falls. The decline in drug blood plasma concentration will continue until the next dose of lorazepam is taken. The drug blood plasma concentration will reach its lowest concentration level, the "Cmin," just before the next dose is administered and absorbed into the blood. That dose causes a rise in blood plasma concentration, and the cycle repeats, reaching the Cmax once again followed by a fall to the Cmin, and administration of the next dose, etc. In contrast to the steady state, the first dose of lorazepam produces different blood plasma values because no lorazepam is in the blood at the time of the dose. The Cmin for such a single dose experiment is zero at the outset. The Cmax is typically noticeably lower than the steady state Cmax. Because the present technology is applicable for chronic administration of lorazepam (for one or more weeks and perhaps months or years), the steady state parameters can be more meaningful. Indeed, in some embodiments, a single dose study (e.g., initial dose) will not provide a therapeutic concentration in the blood stream sooner than 1 hour, often not before 2 hours, and in some embodiments not before 3 hours. In some embodiments, a minimum therapeutic blood plasma concentration can be taken to be 10 ng/ml.

Methods of Use

In another aspect, provided herein are methods of reducing the risks associated with concomitant consumption of lorazepam and alcohol, such as clinical risks that may be associated with such concomitant consumption. The methods comprise preparing or administering an alcohol-resistant oral pharmaceutical composition or dosage form as described herein.

In another aspect, provided herein are methods of inhibiting alcohol extraction of lorazepam from an oral pharmaceutical dosage form, comprising preparing an alcohol-resistant oral pharmaceutical composition or dosage form as described herein.

The following examples are provided by way of illustration and are not intended to be limiting of the invention.

EXAMPLES

Example 1: General Preparation Method

Substrates comprising a controlled release formulation of lorazepam are prepared and provided with an alcohol-resistant coating, such as an ethanol-insoluble film coating. Optionally substrates comprising an immediate release formulation of lorazepam also are prepared and, optionally, provided with a coating, The thickness of the coating is selected and controlled to provide a desired level of alcohol-resistance.

Figure 1:
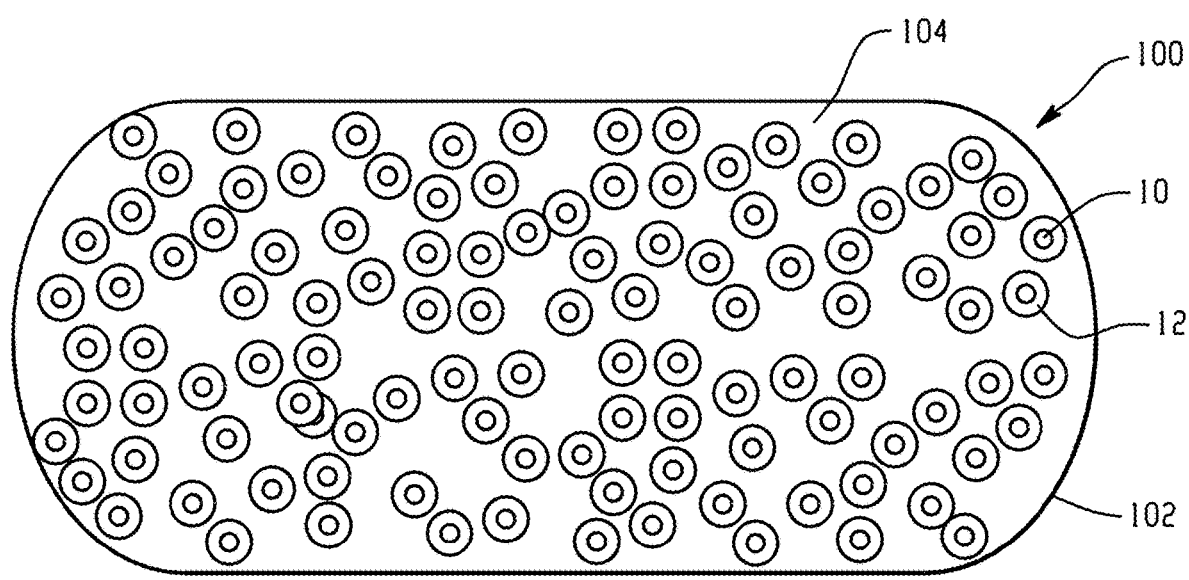
FIG. 1 illustrates non-limiting examples of alcohol-resistant oral pharmaceutical dosage forms as described herein.

As illustrated in FIG. 1, in some embodiments, alcohol-resistant oral pharmaceutical dosage forms as described herein may be in the form of a tablet or capsule (100) that comprises particles, granules, pellets, beadlets, etc. (10) comprising active agent ("API"), wherein individual particles, granules, pellets, beadlets, etc. optionally are provided with an alcohol-resistant coating (12). Additionally or alternatively, in some embodiments, the tablet or capsule is provided with an alcohol-resistant coating (102). As depicted in the figure, the dosage form may be an immediate release dosage form or a controlled release dosage form, depending on the composition of the particles, granules, pellets, beadlets, etc. (10), any additional coatings provided on the particles, granules, pellets, beadlets, etc, the composition of any tablet or matrix (104), and/or any additional coatings provided on the tablet or capsule (100).

Tablets can be prepared by admixing particles, granules, pellets, beadlets, etc. with tabletting excipients and compressing into tablets. As noted above, the compressed tablet matrices optionally are provided with an alcohol-resistant coating, which may be the same as or different from the alcohol-resistant coating on the particles, granules, pellets, beadlets, etc. Additionally or alternatively, the compressed tablet matrices are provided with one or more conventional pharmaceutical coatings, such as seal coatings.

Capsules or sachets can be prepared by filling particles, granules, pellets, beadlets, etc., into capsule shells or sachet packaging. As noted above, capsules optionally are provided with an alcohol-resistant coating, which may be the same as or different from the alcohol-resistant coating on the particles, granules, pellets, beadlets, etc. Additionally or alternatively, the capsules are provided with one or more conventional pharmaceutical coatings, such as seal coatings.

Example 2: Preparation of Alcohol-Resistant Lorazepam Dosage Forms

Sustained release (SR) beadlets comprising lorazepam were prepared in accordance with the formulation set forth in Table 1 below. For some examples, SR beadlets were provided with an alcohol-resistant (AR) coating to obtain AR-coated SR beadlets. For some examples, SR beadlets were provided with a delayed release coating to obtain delayer release (DR) beadlets in accordance with the formulation set forth in Table 2 below. For some examples, DR beadlets prepared in that way were provided with an AR coating to obtain AR-coated DR beadlets. For some examples, SR beadlets were provided with an AR coating prior to being coated with a DR coating.

TABLE 1

Lorazepam Sustained Release (SR) Beadlets

| Raw Materials | % w/w | g/batch |
|---|---|---|
| Lorazepam | 3.0 | 15.0 |
| Hypromellose (K100 premium LV) | 1.0 | 5.00 |
| Pregelatinized maize starch (Starch 1500) | 10.0 | 50.0 |
| Cellulose Microcrystalline (Tabulose 101) | 86.0 | 430.0 |
| Purified Water* | (100) | (500) |
| TOTAL: | 100.0 | 500.0 |

*Not included - removed during the drying process

TABLE 2

Lorazepam Delayed Sustained Release (DR) Beadlets

| Raw Materials | % w/w | g/batch |
|---|---|---|
| Sustained Release Beadlets | 77.1 | 385.5 |
| EUDRAGIT ® FS 30 D | 19.0 | 95.0 |
| PLASACRYL ™ T20 | 1.9 | 9.5 |
| Colloidal silicon dioxide | 2.0 | 10.0 |
| Purified Water* | | |
| TOTAL: | 100.0 | 500.0 |

*Not included—removed during the drying process

The AR coating was an ethanol-insoluble film coating system, based on either sodium carboxymethylcellulose (using OPAGLOS® 2 which includes 54.160% w/w sodium carboxymethylcellulose, 23.890% w/w maltodextrin, 16.950% w/w dextrose monohydrate, and 5.000% w/w stearic acid) or sodium alginate (using PROTANAL® CR 8133 (sodium alginate), PROTANAL® LFR5/60 (sodium alginate) and NS ENTERIC® (99% w/w sodium alginate, 1% w/w stearic acid)). Coating suspensions were sprayed in an Aeromatic Strea-1 fluid bed equipped with a Wurster column. The pump rate was 3 g/min, the inlet temperature 50-65° C. The atomizing air pressure was 1.2±0.2 bar and the air flow rate was controlled in order to maintain a good fluidization. After coating, fluidization was maintained for an additional 5 min as a final drying phase. Lots L055-01046 and L055-01047 were coated by bottom spray Wurster coating with a VFC Lab Micro Flo-Coater equipped with 2.5" Wurster column. Coating parameters are listed in the tables below.

TABLE 3

Coating Parameters

| SR (or DR) Beadlet | AR-Coated SR (or DR) Beadlet | AR Coating Composition (Weight Gain %) |
|---|---|---|
| 1060 | 1061A | NS ENTERIC ® (10%) |
| 1060 | 1061B | NS ENTERIC ® (20%) |
| 1060 | 1061C | NS ENTERIC ® (30%) |
| 1060 | 1061D | NS ENTERIC ® (40%) |
| 1060 | 1064A | PROTANAL ® LFR5/60/SiO$_2$ 90/10 (10%) |
| 1060 | 1064B | PROTANAL ® LFR5/60/SiO$_2$ 90/10 (17.5%) |
| 1060 | 1064C | PROTANAL ® LFR5/60/SiO$_2$ 90/10 (25%) |

TABLE 3-continued

| Coating Parameters | | |
|---|---|---|
| 1067 (DR) | 1068 (AR-DR) | PROTANAL ® LFR5/60/SiO$_2$ 90/10 (17.6%) |
| 1067 (DR) | 1069 (AR-DR) | PROTANAL ® LFR5/60/SiO$_2$ 90/10 (25.3%) |
| 1067 (DR) | 01070 (AR-DR) | NS ENTERIC ® (31%) |

| AR-Coated SR Beadlet | DR-Coated. AR-Coated SR Beadlet* | AR + DR Coating Compositions (Weight Gain %) |
|---|---|---|
| 1061C (with AR coating) | 1062 (with DR coating) | 1.69% drug load beadlets AR: NS ENTERIC ® (30%) + DR: EUDRAGIT ® FS 30D + PLASACRYL ™ T20 (20%) |
| 1064B (with AR coating) | 1065 (with DR coating) | 1.8% drug load beadlets AR: PROTANAL ® LFR5/60/ SiO$_2$ 90/10 (17.5%) + DR: EUDRAGIT ® FS 30D + PLASACRYL ™ T20 (20%) |

*SR beadlets were provided with AR coating prior to DR coating

TABLE 4

Coating Parameters - Alcohol-Resistant SR Enteric Coated Beadlets

| SR Beadlet | DR Beadlet | DR Coating Composition (Weight Gain %) |
|---|---|---|
| 1011 (SR Control) | 1020 (DR Control) | EUDRAGIT ® FS 30D + PLASACRYL ™ T20 (22%) + SiO$_2$ |
| 1047 (AR-SR) | 1051* | EUDRAGIT ® FS 30D + PLASACRYL ™T20 (25%) + SiO$_2$ |
| 1050 (AR-SR) | 1052* | EUDRAGIT ® FS 30D + PLASACRYL ™ T20 (23%) |
| 1056 (AR-SR) | 1057* | EUDRAGIT ® FS 30D + PLASACRYL ™ T20 (21%) + SiO$_2$ |
| 1061C (AR-SR) | 1062* | EUDRAGIT ® FS 30D + PLASACRYL ™ T20 (20%) |
| 1064B (AR-SR) | 1065* | EUDRAGIT ® FS 30D + PLASACRYL ™ T20 (20%) |

*SR beadlets were provided with AR coating prior to DR coating

TABLE 5

Sample Coating Process Parameters

| Parameter | L055-01xxx | | |
|---|---|---|---|
| | 045 | 061A | 064A |
| Batch size (g) | 100 | 50 | 50 |
| Solids concentration in coating liquid (%) | 3 | 4 | 8 |
| Inlet air T (°C.) | 50 | 60 | 60 |
| Outlet air T (°C.) | 35-37 | 46-49 | 40-41 |
| Atomizing air P (bar) | 1.2 | 1.2 | 1.2 |
| Spray rate (g/min) | 3 | 2 | 2 |
| Drying time (min) | 5 | 5 | 5 |
| Actual WG (%) | 5 | 10 | 10 |

Capsules were prepared comprising SR beadlets and DR beadlets, some provided with AR coatings as shown in the table below. The capsules contained a total of 2 mg lorazepam.

TABLE 6

| | 2 mg Capsules | | |
|---|---|---|---|
| Capsule Lot # | SR Beadlet | DR Beadlet | AR Coating |
| 1071 (control) | 1060 | 1067 | none |
| 1072 | 1061C (AR-SR) | 1067 | AR coating only on SR beadlets |
| 1073 | 1064B (AR-SR) | 1067 | AR coating only on SR beadlets |
| 1074 | 1064C (AR-SR) | 01067 | AR coating only on SR beadlets |
| 1075 | 1061C (AR-SR) | 1070 (AR-DR) | AR coating on both beadlet types |
| 1076 | 1064B (AR-SR) | 1068 (AR-DR) | AR coating on both beadlet types |
| 1077 | 1064C (AR-SR) | 01069 (AR-DR) | AR coating on both beadlet types |

Example 3: Evaluation of Alcohol-Resistance Dissolution

Dissolution profiles for select lots from Example 2 were evaluated by assessing dissolution at 37.0±0.5° C. and 100 rpm for two hours in aqueous 0.1 N HCl solution (data not shown). Results indicated that the AR coating did not substantially impact release of the active agent from the substrate when tested in non-alcoholic dissolution media.

Dissolution profiles for select lots from Example 2 were evaluated by assessing dissolution at 37.0±0.5° C. and 100 rpm for two hours in an acidic ethanolic aqueous solution comprising 40% ethanol and 0.1 N HCl solution. Results are reported in Tables 7 and 8 below and in FIG. 2 and FIG. 3. Results also are reported relative to the amount of drug released from an uncoated substrate ("control" or "core"), where relative release (%) in alcohol was calculated by dividing the percent dissolution at 2 hrs for the sample formulation by the percent dissolution at 2 hrs for the control formulation. As illustrated in Table 7 and FIG. 2, several AR-coated SR beadlet formulations released 75% or less active agent as compared to the amount of active agent released from an uncoated (control) SR beadlet formulation, when tested in alcoholic dissolution media.

In a positive control experiment, the uncoated SR beadlet of Table 7 exhibited 37% dissolution at 2 hrs in an ethanol-free dissolution medium versus 81% dissolution at 2 hrs in the 40 ethanol dissolution medium, confirming that uncoated substrate exhibits increased release of active agent in the presence of alcohol. Similarly, the uncoated SR beadlet of Table 8 exhibited 18% dissolution at 2 hrs in an ethanol-free dissolution medium versus 80% dissolution at 2 hrs in the 40 ethanol dissolution medium.

Taken as a whole, these results show that the AR-coated substrates described herein exhibit reduced release in the presence of alcohol as compared to corresponding uncoated substrates, but exhibit similar release in non-alcoholic media. This indicates that the compositions described herein can be used to achieve pharmacokinetic profiles and therapeutic efficacy similar to uncoated compositions when administered without the concomitant use of alcohol, but will exhibit less release when administered concomitantly with alcohol. The data also indicated that the compositions described herein are resistant to alcohol extraction.

TABLE 7

Ethanolic Medium Dissolution of SR Beadlets - Dissolution Acid Stage, 0.1N HCl, 40% Ethanol, 100 rpm

| ID | SR Core | 1061A AR Coated | 1061B AR Coated | 1061C AR Coated | 1061D AR Coated |
|---|---|---|---|---|---|
| Formulation | Control | NS ENTERIC ® (10%) | NS ENTERIC ® (20%) | NS ENTERIC ® (30%) | NS ENTERIC ® (40%) |
| Drug load | 3% | 2.7% | 2.5% | 2.2% | 2.0% |
| Disso Time (hrs) | % Drug Released | | | | |
| 1 | 75 (74-76) | 56 (54-57) | 42 (41-42) | 37 (35-39) | 26 (25-28) |
| 2 | 81 (81-81) | 76 (74-78) | 62 (62-63) | 61 (59-64) | 49 (48-51) |
| % Relative Release* | 100 | 94 | 77 | 75 | 60 |

| ID | 1064A AR Coated | 1064B AR Coated | 1064C AR Coated | 1062 1065 AR Coated |
|---|---|---|---|---|
| Formulation | PROTANAL ® LFR5/60/SiO$_2$ 90/10 (10%) | PROTANAL ® LFR5/60/SiO$_2$ 90/10 (17.5%) | PROTANAL ® LFR5/60/SiO$_2$ 90/10 (25%) | NS ENTERIC ® (30% or 17.5%) EUDRAGIT ® FS30D |
| Drug load | 2.7% | 2.5% | 2.3% | 1.7% 1.8% |
| Disso Time (hrs) | | | | |
| 1 | 53 (51-58) | 30 (28-31) | 18 (17-19) | 10 (8-12) 22 (20-26) |
| 2 | 74 (71-78) | 48 (47-50) | 28 (27-29) | 42 (35-48) 47 (45-50) |
| % Relative Release* | 91 | 59 | 35 | 52 58 |

*Relative to control SR core at 2 hrs.

TABLE 8

Ethanolic Medium Dissolution of Capsule Lots - Dissolution Acid Stage, 0.1N HCl, 40% Ethanol, 100 rpm

| ID | 1071 | 1072 | 1073 | 1074 | 1075 | 1076 | 1077 |
|---|---|---|---|---|---|---|---|
| Formulation | Control | 1061C + DR Beadlets | 1064B + DR Beadlets | 1064C + DR Beadlets | 1061C + 1070 Beadlets | 1064B + 1068 Beadlets | 1064C + 1069 Beadlets |
| Drug load | 2 mg | 2 mg | 2 mg | 2 mg | 2 mg | 2 mg | 2 mg |
| Disso Time (hrs) | % Drug Released | | | | | | |
| 1 | 67 (66-67) | 44 (43-45) | 38 (37-39) | 33 (32-33) | 36 (35-37) | 25 (24-25) | 15 (14-15) |
| 2 | 80 (80-81) | 69 (68-70) | 59 (57-60) | 51 (50-51) | 62 (61-63) | 44 (43-45) | 29 (28-29) |
| % Relative Release* | 100 | 86 | 74 | 64 | 78 | 55 | 36 |

*Relative to control capsule at 2 hrs

What is claimed is:

1. An alcohol-resistant controlled release oral pharmaceutical composition of lorazepam, comprising
   (A) alcohol-resistant coated sustained release beadlets comprising (i) beadlets comprising lorazepam and a controlled release polymer in a sustained release formulation surrounded by an alcohol-resistant coating; and
   (B) alcohol-resistant coated delayed sustained release beadlets comprising (i) beadlets comprising lorazepam and a controlled release polymer in a sustained release formulation, (ii) an enteric coating surrounding the beadlets, and (iii) an alcohol-resistant coating surrounding the beadlets, and wherein the alcohol-resistant coating may be interior to or exterior to the enteric coating;
   wherein the alcohol-resistant coating comprises one or more ethanol-insoluble components selected from the group consisting of carbomers, polyethylene oxide polymers, xanthan gum, and alginate;
   wherein the amount of lorazepam released from the alcohol-resistant coated sustained release beadlets and alcohol-resistant coated delayed sustained release beadlets is 75% or less than the amount of lorazepam released from the corresponding beadlets without the alcohol-resistant coating, when measured by dissolution testing at 37.0±0.5° C. and 100 rpm for two hours in an acidic ethanolic aqueous solution comprising 40% ethanol and 0.1 N HC1 solution in accordance with USP <711>, and
   wherein the amount of lorazepam released from the alcohol-resistant coated sustained release beadlets and alcohol-resistant coated delayed sustained release beadlets is ±25% or less as compared to the amount of lorazepam released from a corresponding beadlets without the alcohol-resistant coating, when measured by dissolution testing at 37.0±0.5° C. and 100 rpm for two hours in an aqueous 0.1 N HC1 solution, in accordance with USP <711>.

2. The composition of claim 1, wherein the alcohol-resistant coating comprises sodium alginate.

3. The composition of claim 1, wherein the alcohol-resistant coating comprises xanthan gum.

4. The composition of claim 1, wherein the weight:weight ratio of alcohol-resistant coating to beadlets comprising lorazepam and a controlled release polymer in a sustained release formulation is at least 1:10.

5. The composition of claim 4, wherein the weight:weight ratio of alcohol-resistant coating to beadlets comprising lorazepam and a controlled release polymer in a sustained release formulation is from 1:10 to 3:1.

6. The composition of claim 4, wherein the weight:weight ratio of alcohol-resistant coating to beadlets comprising lorazepam and a controlled release polymer in a sustained release formulation is from 1:10 to 1:1.

7. The composition of claim 4, wherein the weight:weight ratio of alcohol-resistant coating to beadlets comprising lorazepam and a controlled release polymer in a sustained release formulation is selected from the group consisting of at least 1:10, at least 1.5:10, at least 2:10, at least 2.5:10, at least 3:10, at least 3.5:10, at least 4:10, at least 4.5:10, at least 5:10, at least 5.5:10, at least 6:10, at least 6.5:10, at least 7:10, at least 7.5:10, at least 8:10, at least 8.5:10, at least 9:10, at least 9.5:10, and at least 1:1.

8. The composition of claim 1, wherein the alcohol-resistant coated sustained release beadlets release less than 50% by weight of lorazepam in the presence of alcohol as compared to the amount of lorazepam released by a corresponding beadlets without the alcohol-resistant coating, when measured by dissolution testing at 37.0±0.5° C. and 100 rpm for two hours in an acidic ethanolic solution comprising 40% ethanol and 0.1 N HC1 solution.

9. The composition of claim 1, wherein the alcohol-resistant coated sustained release beadlets release less than 40% by weight of lorazepam in the presence of alcohol as compared to the amount of lorazepam released by a corresponding beadlets without the alcohol-resistant coating, when measured by dissolution testing at 37.0±0.5° C. and 100 rpm for two hours in an acidic ethanolic solution comprising 40% ethanol and 0.1 N HC1 solution.

10. The composition of claim 1, wherein the alcohol-resistant coated sustained release beadlets release less than 25% by weight of lorazepam in the presence of alcohol as compared to the amount of lorazepam released by a corresponding beadlets without the alcohol-resistant coating, when measured by dissolution testing at 37.0±0.5° C. and 100 rpm for two hours in an acidic ethanolic solution comprising 40% ethanol and 0.1 N HC1 solution.

11. The composition of claim 1, wherein the alcohol-resistant coated sustained release beadlets release less than 10% by weight of lorazepam in the presence of alcohol as compared to the amount of lorazepam released by a corresponding beadlets without the alcohol-resistant coating, when measured by dissolution testing at 37.0±0.5° C. and 100 rpm for two hours in an acidic ethanolic solution comprising 40% ethanol and 0.1 N HC1 solution.

12. The composition of claim 1, wherein the alcohol-resistant coated sustained release beadlets release less than 1% by weight of lorazepam in the presence of alcohol as compared to the amount of lorazepam released by a corresponding beadlets without the alcohol-resistant coating, when measured by dissolution testing at 37.0±0.5° C. and 100 rpm for two hours in an acidic ethanolic solution comprising 40% ethanol and 0.1 N HC1 solution.

13. The composition of claim 1, wherein the composition is in a form selected from the group consisting of tablets and capsules.

14. The composition of claim 1, wherein the alcohol-resistant coating of the alcohol-resistant coated delayed sustained release beadlets is exterior to the enteric coating.

15. The composition of claim 1, wherein the alcohol-resistant coating of the alcohol-resistant coated delayed sustained release beadlets is interior to the enteric coating.

16. The composition of claim 1, wherein the alcohol-resistant coated sustained release beadlets and alcohol-resistant coated delayed sustained release beadlets are formulated in a tablet or filled into a capsule shell, and wherein the tablet or capsule shell optionally is surrounded by an alcohol-resistant coating.

17. The composition of claim 1, wherein the alcohol-resistant coated sustained release beadlets and alcohol-resistant coated delayed sustained release beadlets are formulated as a tablet or capsule surrounded by an alcohol-resistant coating.

18. The composition of claim 1, wherein the alcohol-resistant coated sustained release beadlets and alcohol-resistant coated delayed sustained release beadlets are contained within a sachet package.

19. The composition of claim 1, further comprising lorazepam in an immediate release component.

20. A method of reducing the risks of concomitant consumption of lorazepam and alcohol, comprising administering an alcohol-resistant oral pharmaceutical composition according to claim 1 to a subject in need thereof.

21. A method of inhibiting alcohol extraction of lorazepam from an oral pharmaceutical composition, comprising preparing an alcohol-resistant oral pharmaceutical composition according to claim 1.

22. The composition of claim 1, wherein the amount of lorazepam released from the alcohol-resistant coated sustained release beadlets and alcohol-resistant coated delayed sustained release beadlets is ±20% or less as compared to the amount of lorazepam released from a corresponding beadlets without the alcohol-resistant coating, when measured by dissolution testing at 37.0±0.5° C. and 100 rpm for two hours in an aqueous 0.1 N HCl solution, in accordance with USP <711>.

23. The composition of claim 1, wherein the amount of lorazepam released from the alcohol-resistant coated sustained release beadlets and alcohol-resistant coated delayed sustained release beadlets is ±10% or less as compared to the amount of lorazepam released from a corresponding beadlets without the alcohol-resistant coating, when measured by dissolution testing at 37.0±0.5° C. and 100 rpm for two hours in an aqueous 0.1 N HCl solution, in accordance with USP <711>.

24. The composition of claim 1, wherein the amount of lorazepam released from the alcohol-resistant coated sustained release beadlets and alcohol-resistant coated delayed sustained release beadlets is ±5% or less as compared to the amount of lorazepam released from a corresponding beadlets without the alcohol-resistant coating, when measured by dissolution testing at 37.0±0.5° C. and 100 rpm for two hours in an aqueous 0.1 N HCl solution, in accordance with USP <711>.

25. The composition of claim 1, wherein the amount of lorazepam released from the alcohol-resistant coated sustained release beadlets and alcohol-resistant coated delayed sustained release beadlets is ±1% or less as compared to the amount of lorazepam released from a corresponding beadlets without the alcohol-resistant coating, when measured by dissolution testing at 37.0±0.5° C. and 100 rpm for two hours in an aqueous 0.1 N HCl solution, in accordance with USP <711>.

* * * * *